United States Patent [19]

Wagner et al.

[11] Patent Number: 4,533,677
[45] Date of Patent: Aug. 6, 1985

[54] HYPOGLYCEMIC N-(2-SUBSTITUTED-3-DIALKYLAMINO-2-PROPENYLIDENE)-N-ALKYLALKANAMINIUM SALTS

[75] Inventors: Eugene R. Wagner, Carmel; Charlotte L. Barney; Donald P. Matthews, both of Indianapolis, all of Ind.

[73] Assignee: Merrell Dow Pharmaceuticals Inc., Cincinnati, Ohio

[21] Appl. No.: 494,741

[22] Filed: May 16, 1983

[51] Int. Cl.³ ............................................. A61K 31/13
[52] U.S. Cl. .................................. 514/638; 514/466; 514/641
[58] Field of Search ................ 564/279; 424/325, 330, 424/282

[56] References Cited

FOREIGN PATENT DOCUMENTS 2317230 10/1973 Fed. Rep. of Germany .

OTHER PUBLICATIONS

Conant, James Bryant, et al., *The Chemistry of Organic Compounds*, 4th Ed. (1955), at p. 335, The MacMillan Co., Publ.
Gran, Walter Chemical Abstracts, vol. 86, (1977), #155,104m.
Kucera, J., et al., *Coll. Czech. Chem Commun.*, vol. 32, (1967), pp. 1704–1711.
B. Rada, A. Luczak, A. Holy and Z. Arnold, Chemotherapy 20, 141–147, (1974).
C. Jutz, R. Kirchlechner and H. J. Seidel, Chem. Ber. 102 (7), 2301–2318, (1969).
A. Holy and Z. Arnold, Coll. Czech. Chem. Commun. 38(5), 1371–1380, (1973).
Z. Arnold, Coll. Czech Chem. Commun. 38(4), 1168–1172, (1973).
C. Jutz, R. M. Wagner and H. G. Loebering, Angew. Chem. Int. Ed. in English 13, 737–739, (1974).
C. Jutz and E. Schweiger, Chem. Ber. 107(7), 2383–2396, (1974).
C. Jutz, R. M. Wagner, A. Kraatz and H. G. Loebering, Justus Liebigs Ann. Chem. 1975(5), 874–900.
H. Lee, N. Shyamasundar and R. G. Harvey, J. Org. Chem. 46(4), 2889–2895, (1981).
C. Jutz, H. G. Loebering and K. H. Trinkl, Synthesis 1977(5), 326–328.
C. Jutz and H. G. Peuker, Synthesis 1975(7), 431–433.

*Primary Examiner*—Natalie Trousof
*Assistant Examiner*—L. Hendriksen
*Attorney, Agent, or Firm*—Edlyn S. Simmons; Gary D. Street; Raymond A. McDonald

[57] ABSTRACT

N-(3-Dialkylamino-2-propenylidene)-N-alkylalkanaminium salts substituted in the 2-position with an ether or thioether and having the formula

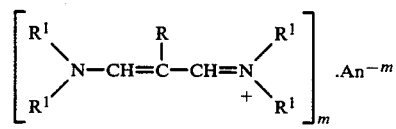

are active as hypoglycemic agents.

9 Claims, No Drawings

HYPOGLYCEMIC N-(2-SUBSTITUTED-3-DIALKYLAMINO-2-PROPENYLIDENE)-N-ALKYLALKANAMINIUM SALTS

BACKGROUND OF THE INVENTION

Hyperglycemia, an abnormally elevated level of blood sugar, is the primary symptom of *diabetes mellitus*, a metabolic disease characterized by inadequate response to insulin or inadequate secretion of insulin from the islets of Langerhans of the pancreas. Control of elevated blood sugar levels may be achieved through injection of insulin or by administration of pharmaceutical hypoglycemic agents, usually by the oral route. The majority of known hypoglycemic agents are sulfonylureas, such as chlorpropamide and tolazamide, and biguanides, such as phenformin.

It has now been discovered that certain N-(2-substituted-3-aminopropenylidene)alkanaminium salts are active as oral hypoglycemic agents. Several of these compounds are known to the prior art. With the exception of a study by Rada, et al., (*Chemotherapy* 20, 141–7 (1974)), in which N-(3-(dimethylamino)-2-ethoxy-2-propenylidene)-N-methylmethanaminium perchlorate was tested unsuccessfully for antiviral activity, however, it has not previously been suggested that the N-(2-substituted-3-aminopropenylidene)alkanaminium salts of the present invention have any biological activity.

SUMMARY OF THE INVENTION

The present invention relates to a method of lowering the blood sugar level of a hyperglycemic mammal by administering internally to said mammal a hypoglycemically effective amount of a N-(2-substituted-3-amino-2-propenylidene)alkanaminium salt of general formula I

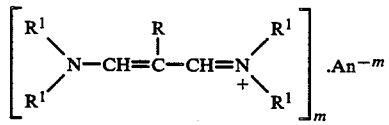

wherein R represents a group of formula $R^3X$; $R^1$ represents methyl or ethyl; $R^3$ represents straight or branched alkyl of from 1 to 12 carbon atoms, straight or branched alkenyl of from 2 to 12 carbon atoms, cycloalkyl of from 3 to 8 carbon atoms, cycloalkylalkyl of from 4 to 10 carbon atoms, optionally substituted phenyl or benzyl; X is an oxygen atom or a divalent sulfur atom; An is a pharmaceutically acceptable anion; and m represents the valence of the anion.

The present invention also relates to novel hypoglycemic agents of general formula II

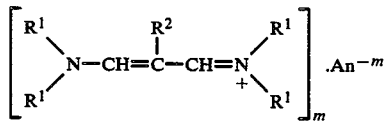

wherein $R^2$ represents a group of formula $R^3S-$ or $R^4O-$, in which $R^1$, $R^3$, m and An have the meanings defined above and $R^4$ represents cycloalkyl from 3 to 8 carbon atoms, straight or branched chain alkyl or alkenyl of from 3 to 12 carbon atoms or cycloalkylalkyl of from 4 to 10 carbon atoms.

The novel compounds of formula II are markedly active as glucose lowering agents.

DETAILED DISCLOSURE OF THE INVENTION

As used herein, the term alkyl embraces straight and branched chain alkyl moieties of from 1 to 12 carbon atoms, for example, methyl, ethyl, propyl, isopropyl, n-butyl, 1-methylpropyl, n-pentyl, 3-methylbutyl, n-hexyl, n-heptyl, 3-ethylpentyl 1-methylundecyl and n-octyl. Optionally substituted phenyl refers to unsubstituted phenyl, to phenyl substituted by from one to three groups selected from lower alkyl, lower alkoxy, halogen, hydroxy, benzyloxy, di(lower alkyl)amino, nitro, phenyl or benzyl, wherein lower alkyl and lower alkoxy include straight and branched alkyl chains of from 1 to 4 carbon atoms and halogen includes bromine, chlorine, fluorine and iodine, and to phenyl substituted by a single 2,3- or 3,4-methylenedioxy moiety. Pharmaceutically acceptable anions include, for example, inorganic anions, such as perchlorate, chloride, bromide, iodide, nitrate and sulfate, carboxylic acid anions, such as acetate, citrate and maleate, and sulfonic acid anions, such as methanesulfonate, camsylate and toluene sulfonate. Notable among the salts suitable for these hypoglycemic agents are the iodides and the 2-oxo-10-bornanesulfonate or camsylate salts disclosed and claimed in an application Ser. No. 494,742 entitled HYPOGLYCEMIC N-(2-SUBSTITUTED-3-DIALKYLAMINO-2-PROPENYLIDENE)-N-ALKYLALKANAMINIUM CAMSYLATE SALTS of Samuel S. M. Wang, filed on even date herewith.

Compounds of the present invention are suitable for treatment of diabetes mellitus or for lowering elevated blood glucose levels resulting from other disorders, such as pancreatitis. They may be administered alone or in compositions incorporating art-recognized excipients by the oral, subcutaneous, intravenous or intraperitoneal route. Preferably, the compounds are administered orally.

The effective hypoglycemic amount of the active compounds to be internally administered to a mammal, that is the amount which is effective to significantly lower the amount of sugar in the blood, can vary depending upon such factors as the particular N-(2-substituted-3-amino-2-propenylidene)alkanaminium salt employed, the severity of the diseaae, the desired level of blood sugar to be obtained, the period of administration and the method of administration. In general, an effective daily dosage range is from about 1 to about 750 mg/kg of body weight with a daily dosage range of from about 50 to 500 mg/kg of body weight, in a single or divided oral dose, being preferred. Suitable dosage forms may be prepared by following the conventional techniques of the pharmacist. The compounds of general formula I together with suitable pharmaceutical carriers can be in the form of conventional solid unit dosage forms such as tablets or capsules, or embedded in a polymeric matrix for sustained release. In the preparation of solid unit dosage forms it may be desirable to micronize the compound to be employed. In solid unit dosage forms the compounds can be combined with conventional carriers, for example, binders, such as acacia, corn starch or gelatin; disintegrating agents, such as corn starch, guar gum, potato starch or alginic acid; lubricants, such as stearic acid or magnesium stearate; and inert fillers, such as lactose, sucrose, corn starch, cellulose, or synthetic polymers, such as polyvinylpyrrolidone.

The compounds of general formula I may also be administered as liquid suspensions or solutions using a sterile liquid, such as an oil, water, an alcohol, or mixtures thereof, with or without the addition of a pharmaceutically suitable surfactant, suspending agent, or emulsifying agent. Water, saline, aqueous sucrose and related sugar solutions, alcohol and glycerols, and polyethers, such as polyethyleneglycol, may be employed in the preparation of liquid formulations which may suitably contain suspending agents, such as pectin, carbomers, methyl cellulose, hydroxypropyl cellulose or carboxymethyl cellulose, as well as buffers and preservatives.

The reduction of raised blood glucose levels by a compound of general formula I is demonstrated by the following experimental data. Male Swiss mice, weighing at least 30 grams, were fasted for 18–24 hours and injected intraperitoneally with a measured amount of a 0.6% solution of a compound of general formula I in a 0.5% aqueous methylcellulose solution. After 15 minutes a 1 molar solution of L-alanine (pH 7.21) was injected intraperitoneally in an amount calculated to provide 0.1 ml/10 g body weight. After an additional 30 minutes, the mice were sacrificed and the blood collected. The serum was then analyzed for blood glucose according to standard laboratory methods and the blood glucose level of the animals given a test compound was compared with the blood glucose level of control animals given only L-alanine. A ratio representing the reduction of the L-alanine induced blood glucose increase due to administration of a test compound serves as a measure of the effectiveness of the test compound. The percentage of serum glucose lowering is calculated according to the formula $$\text{\% Serum Glucose Lowering} = \frac{\text{(alanine control)} - \text{(alkanaminium treated)}}{\text{(alanine control)} - \text{(fasted control)}} \times 100$$

wherein the quantities in parentheses represent serum glucose concentrations expressed in uniform units. Thus, a blood glucose level in a treated mouse identical to that of a fasted control would give a Serum Glucose Lowering of 100%. The results of tests of various compounds of general formula I administered in a 15 mg/kg dose are tabulated below.

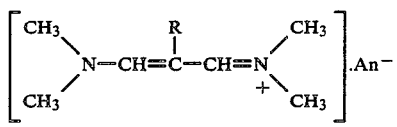

| R | An | % Serum Glucose Lowering |
|---|----|--------------------------|
| C₂H₅S— | ClO₄ | 139 |
| n-C₃H₇S— | ClO₄ | 228 |
| n-C₄H₉S— | ClO₄ | 187 |
| s-C₄H₉S— | ClO₄ | 255 |
| cyclohexylthio | ClO₄ | 128 |
| phenylthio | ClO₄ | 217 |
| benzylthio | ClO₄ | 389 |
| n-C₃H₇O— | I | 183 |
| n-C₃H₇O— | camsylate | 337 |
| n-C₆H₁₃O— | ClO₄ | 358 |
| cyclohexyloxy | ClO₄ | 247 |
| cyclopropylmethoxy | ClO₄ | 232 |

-continued

| R | An | % Serum Glucose Lowering |
|---|----|--------------------------|
| phenoxy | ClO₄ | 251 |

The novel compounds of general formula Ia, which are compounds of formula I wherein X is a divalent sulfur atom are prepared by reaction of an R³-substituted sulfenyl bromide, with an appropriate dialkylaminoacrolein and subsequent reaction of the resulting 3-(dialkylamino)-2-(R³-thio)-2-propenal with an appropriate dialkylcarbamoyl halide, for example, a dialkylcarbamoyl chloride, and with a salt of the desired anion, as shown in Reaction Scheme A, wherein R¹ and R³ have the meanings defined above.

Reaction Scheme A

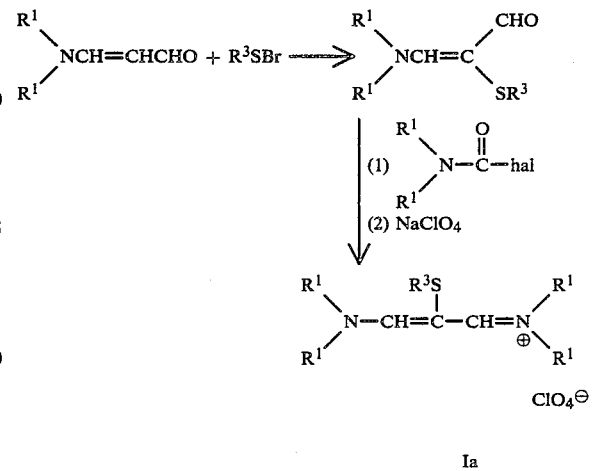

Ia

Dialkylaminoacroleins and dialkylcarbamoyl halides used as intermediates in the synthesis of compounds of formula Ia are well known and may be obtained from commercial sources or prepared by methods well known to the prior art.

R³-Sulfenyl bromides of formula R³SBr are also well known to the prior art. For use as intermediates in the preparation of a compound of formula Ia, a compound for formula R³SBr is preferably generated in situ by reaction of an R³-disulfide of formula R³SSR³ with bromine. Approximately one equivalent of bromine is added to the disulfide, which is dissolved in an appropriate solvent, for example, a chlorinated hydrocarbon such as methylene chloride, and reacted under an inert atmosphere, such as nitrogen or argon, at a reduced temperature, for example, from about −10° to 10° C., for from about 5 to about 20 minutes.

Following the formation of the R³-sulfenyl bromide, a solution of 3-dialkylaminoacrolein and a base, for example, an organic base such as triethylamine, in a suitable solvent, such as methylene chloride, is added gradually with continued cooling. When the exothermic reaction subsides, the reaction mixture is permitted to warm gradually to room temperature. The reaction mixture is then extracted with water and the organic layer concentrated to give crude 3-(dialkylamino)-2-(R$^3$-thio)-2-propenal, which is then purified by standard methods, for example, by preparative high pressure liquid chromatography, using an appropriate solvent such as ethyl acetate.

The 3-(dialkylamino)-2-(R$^3$-thio)-2-propenal is mixed with an excess of dialkylcarbamoyl halide in an appropriate organic solvent, for example, benzene, and stirred at room temperature for from about 1 to about 7 days. The reaction mixture is extracted with water and the aqueous layer charged with an excess of an inorganic salt to yield a compound of formula Ia. The preferred salt for preparation of a compound of formula II is sodium perchlorate, which yields the perchlorate salt of formula Ia.

General methods suitable for preparing compounds of formula I wherein R is OR$^3$ have been described in the prior art, for example, by Z. Arnold, *Collection Czech. Commun.*, 38, 1168–72 (1973), which is incorporated herein by reference. Compounds of formula I wherein R is R$^3$O are prepared by reacting a mixed acetal of formula III with a Vilsmeier-Haack reagent and quenching the reaction with aqueous sodium perchlorate, as shown in Reaction Scheme B.

Reaction Scheme B

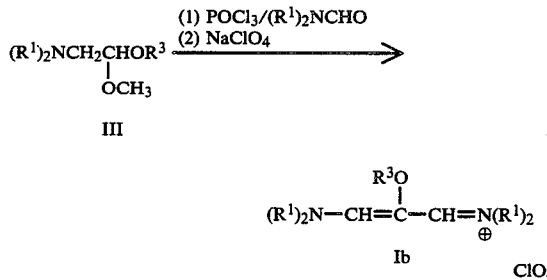

III $$(R^1)_2N-CH=\overset{\overset{R^3O}{|}}{C}-CH=\overset{\oplus}{N}(R^1)_2$$

Ib

ClO$_4^\ominus$

In Reaction Scheme B, R$^1$ and R$^3$ have the meanings defined above.

General methods for performing the Vilsmeier-Haack reaction are well known to the prior art. For the preparation of the compounds of general formula Ib, phosphoryl chloride is added to the dialkylformamide and the mixed acetal of formula III added gradually, maintaining a temperature during addition of about 90°–100° C. The product is then isolated by pouring the cooled solution into cooled aqueous solution of an appropriate salt, such as sodium perchlorate, to yield the perchlorate salt of formula Ib.

The mixed acetal of formula III may be prepared by methods analogous to those used for the preparation of previously known mixed acetals. For example, an alcohol of formula R$^3$OH may be reacted with N-bromosuccinimide (NBS) and methyl vinyl ether in an appropriate solvent, for example, a chlorinated hydrocarbon such as carbon tetrachloride or methylene chloride, at a temperature of from about −10° to 10° C., to produce a bromoethane acetal of the formula BrCH$_2$CH(OCH$_3$)OR$^3$. Upon completion of the reaction, as indicated by vapor phase chromatography, the reaction mixture is filtered and the solvent evaporated. The bromoethyl acetal is dissolved in an appropriate solvent, for example, dimethylformamide or ethyl ether, chilled to about −10° to 10° C, and an excess, for example, 2 to 3 equivalents, of a dialkylamine of formula NH(R$^1$)$_2$ added with stirring. The reaction mixture is permitted to warm to ambient temperature and stirring is continued for from about 8 hours to about 10 days, until the reaction is complete. The resulting dialkylaminoethyl acetal of formula III is isolated by extraction into an appropriate solvent, for example, a hydrocarbon such as hexane, and evaporation of the solvent.

Where R$^1$ is methyl, the dialkylformamide of formula (R$^1$)$_2$NCHO which is employed in the performance of the Vilsmeier-Haack reaction according to Reaction Scheme B is dimethylformamide. Compounds of formula I wherein R$^1$ is ethyl may be prepared by using diethylformamide for preparation of the Vilsmeier-Haack reagent or by refluxing a compound of formula I wherein R$^1$ is methyl with diethylamine and p-toluenesulfonic acid for from about 1 to about 4 hours in a suitable solvent, such as ethanol.

Compounds of formula I, prepared according to the methods disclosed hereinabove, may be purified by art-recognized methods, especially by recrystallization from a suitable solvent or from a combination of solvents. Suitable solvents for the recrystallization of a compound of formula I include alcohols, such as methanol, ethanol and isopropanol; esters, such as ethylacetate; ketones, such as acetone or butanone; nitriles, such as acetonitrile; and mixtures of such solvents with water or with an aromatic hydrocarbon, such as toluene.

When a pharmaceutically acceptable anion other than the perchlorate anion is desired, the compounds of formula I may be subjected to any suitable anion exchange method. For example, a commercially available anion exchange resin, for example, a column containing Dowex ®1-8X resin, a polymeric resin manufactured by The Dow Chemical Company, may be washed with an aqueous solution of an acid yielding the desired anion, and a solution of the perchlorate salt in an aqueous solvent, for example, aqueous ethanol, poured through the resin. The eluted solution, containing the salt of formula I with the desired anion, is concentrated by evaporation and recrystallized. Alternatively, the perchlorate salt of formula I may be dissolved by heating in an appropriate anhydrous solvent, such as absolute alcohol, adding a concentrated aqueous solution of an alkali metal camsylate or iodide to the warm solution, and stirring to form a clear solution. The solution is sonified to ensure complete precipitation, additional anhydrous solvent is added, and the solution is cooled to precipitate alkali metal perchlorate salt, which is removed by filtration. The solution of formula I camsylate or iodide is concentrated by evaporation and purified by art-recognized methods of extraction and recrystallization. A preferred method of anion exchange is to stir a solid methanaminium perchlorate salt of formula I with an alkali metal salt of the desired anion for about 1 to 2 hours, using an excess, for example, from 1 to 2 mole equivalents, of the alkali metal salt. During stirring, water insoluble alkali metal perchlorate is precipitated and may be removed by filtration, leaving an aqueous solution of the salt of formula I bearing the desired anion. The solution is extracted into a suitable solvent, for example, a chlorinated hydrocarbon such a methylene chloride, preferably after addition of an additional amount, for example, 1 equivalent, of the alkali metal salt. The extract is then dried and recrystallized from an appropriate solvent.

Methods for the preparation of compounds of general formula I and suitable compositions for the administration thereof are further illustrated by the following examples.

EXAMPLE 1

Preparation of N-(3-(dimethylamino)-2-(n-propylthio)-2-propenylidene-N-methylmethanaminium perchlorate A methylene chloride solution of 21 g (0.14 mol) n-propyl disulfide (Fairfield Chem. Co.) was cooled to −10° C. and charged with 22.4 g (0.14 mol) bromine. After 15 minutes, a mixture of 25 ml triethylamine, 23 g (0.23 mol) 3-dimethylaminoacrolein, 100 ml methylene chloride was added dropwise while the temperature was held below 0° C. After the addition was completed, the reaction was stirred for 3 hours as the reaction warmed to room temperature. The reaction was shaken twice with 300 ml water, dried ($Na_2SO_4$), and concentrated to give 34.5 g dark oil. This oil was purified by preparative HPLC (EtOAc) to give 25 g 3-(dimethylamino)-2-(n-propylthio)-3-propenal.

A mixture of 19.5 g (0.113 mol) 3-(dimethylamino)-2-(n-propylthio)-2-propenal, 13.9 g (0.13 mol) dimethylcarbamyl chloride and 50 ml benzene was stirred at room temperature. After 3 days, the reaction was extracted with water. The aqueous layer was treated with 15 g $NaClO_4.H_2O$, and the tan solid precipitate was collected and dried. After recrystallization from toluene/isopropanol, 19.3 g (57%) N-(3-(dimethylamino)-2-(propylthio)-2-propenylidene)-N-methylmethanaminium perchlorate was obtained as a buff solid. M.p. 73°–74° C.

EXAMPLE 2

Preparation of N-(3-(dimethylamino)-2-(n-propylthio)-2-propenylidene)-N-methylmethanaminium iodide A 25 g (0.083 mol) sample of the product of Example 1 was dissolved in methylene chloride and shaken vigorously with 75 g KI/200 ml water (2x). The methylene chloride layer was dried ($Na_2SO_4$) and then concentrated to give a white solid, which was recrystallized from 250 ml isopropanol to give 16.5 g (61%) N-(3-(dimethylamino)-2-(n-propylthio)-2-propenylidene)-N-methylmethanaminium iodide. M.p. 168°–171° C.

EXAMPLE 3

Preparation of N-(3-(dimethylamino)-2-(phenylthio)-2-propenylidene)-N-methylmethanaminium perchlorate A methylene chloride solution of 32.75 g (0.15 mol) phenyl disulfide was cooled to 0° C. under nitrogen and 23.9 g (0.15 mol) bromine was added neat. After 10 minutes a solution of 50 ml triethylamine, 100 ml methylene chloride and 25 g (0.25 mol) 3-dimethylaminoacrolein (Fluka CHem. Co.) was added dropwise with cooling to hold the temperature at 0° C. The reaction was allowed to warm to room temperature overnight, shaken with 200 ml water (2x), and the organic layer dried ($Na_2SO_4$) and concentrated to give 49.5 g crude 3-(dimethylamino)-2-(phenylthio)-2-propenal. This aldehyde was purified by preparative HPLC (EtOAc) to give 20.2 g pure aldehyde.

A 17.5 g (0.085 mol) sample of 3-(dimethylamino)-2-(phenylthio)-2-propenal was mixed with 10.7 g (0.1 mol) dimethylcarbamyl chloride and 60 ml benzene. The reaction was stirred at room temperature for 3 days and extracted with 100 ml water. The aqueous layer was charged with 15 g $NaClO_4.H_2O$ and the precipitate collected and dried. After recrystallization (1:1 $CH_3OH/C_2H_5OH$), 9.5 g (49%) N-(3-(dimethylamino)-2-phenylthio)-2-propenylidene-N-methylmethanaminium perchlorate was obtained as a light orange solid. M.p. 134°–136° C.

EXAMPLE 4

When, in the procedure of Example 1, the listed intermediate disulfide was substituted for propyldisulfide, the named perchlorate salt was produced.

| Product | Intermediate Disulfide | Melting Point, °C. |
|---|---|---|
| (a) N—(3-(Dimethylamino)-2-methylthio-2-propenylidene)-N—methylylmethanaminium perchlorate | Methyl disulfide | 84.5–85.5 |
| (b) N—(3-(Dimethylamino)-2-ethylthio-2-propenylidene)-N—methylmethanaminium perchlorate | Ethyl disulfide | oil |
| (c) N—(3-(Dimethylamino)-2-isopropylthio-2-propenylidene)-N—methylmethanaminium perchlorate | Isopropyl disulfide | oil |
| (d) N—(3-(Dimethylamino)-2-butylthio-2-propenylidene)-N—methylmethanaminium perchlorate | Butyl disulfide | room temperature |
| (e) N—(3-(Dimethylamino)-2-(1-methylpropylthio)-2-propenylidene)-N—methylmethanaminium perchlorate | Sec-butyl disulfide | low |
| (f) N—(3-(Dimethylamino)-2-pentylthio-2-propenylidene)-N—methylmethanaminium perchlorate | Pentyl disulfide | oil |
| (g) N—(3-(Dimethylamino)-2-cyclohexylthio-2-propenylidene)-N—methylmethanaminium perchlorate | Cyclohexyl disulfide | 130–132 |
| (h) N—(3-(Dimethylamino)-2-phenylmethylthio-2-propenylidene)-N—methylmethanaminium perchlorate | Benzyl disulfide | 175–177 |
| (i) N—(3-(Dimethylamino)-2-(4-methylphenylthio)-2-propenylidene)-N—methylmethanaminium perchlorate | 4-Methylphenyl disulfide | 112–113 |

EXAMPLE 5

Preparation of N-(3-(dimethylamino)-2-ethoxy-2-propenylidene)-N-methylmethanaminium perchlorate A solution of 1293 g (17.7 mol) dimethylformamide and 1800 ml chloroform was cooled to 3° C. and 910 ml (9.76 mol) phosphorus oxychloride was added at the rate of 10 ml/minute. The resulting mixture was stirred for 30 minutes. N,N-Dimethylaminoacetaldehyde diethyl acetal, 727.9 g (4.51 mol), was added at the rate of 12–15 ml per minute, maintaining the temperature between 6° to 15° C. The mixture was heated at reflux for 3½ hours, then allowed to stir overnight.

The mixture was poured into 4800 g of ice and 3 l hexane and this mixture was agitated, and the organic phase separated and washed with 500 ml cold water. The combined aqueous phases were treated with 1091 g sodium perchlorate, monohydrate, and dissolved in 750 ml distilled water.

Combination of the first and second crops gave 900 g (73.3%) of N-(3-(dimethylamino)-2-ethoxy-2-propenylidene)-N-methylmethanaminium perchlorate, which could be purified by recrystallization from ethanol. M.p. 117°–120° C.

EXAMPLE 6
Preparation of N-(3-(dimethylamino)-2-ethoxy-2-propenylidene)-N-methylmethanaminium nitrate A 4.5'×4" column was packed with 5 l Dowex ®1-8X resin in the chloride form. The column was converted to the nitrate form by eluting the column with sodium nitrate, 2295 g (27 mol), dissolved in 22.9 l distilled water, at a rate of 100 ml/minute. The column was then rinsed with 20 l distilled water, treated with 5 l 75% aqueous ethanol, then treated with 5 l 50% aqueous ethanol. The packing was removed from the column and slurried in 25% aqueous ethanol.

A 292 g (1.08 mol) sample of the product of Example 5 was dissolved in 1.2 l 25% aqueous ethanol at 40° C. The mixture was placed on the column at a rate of 100 ml/minute. The first 500 ml of eluant was discarded. The next 2.0 l of eluant was collected and concentrated under reduced pressure to give 254 g N-(3-(dimethylamino)-2-ethoxy-2-propenylidene)-N-methylmethanaminium nitrate, which could be purified by recrystallization from acetone. M.p. 123°–125° C.

EXAMPLE 7
Preparation of N-(3-(dimethylamino)-2-ethoxy-2-propenylidene)-N-methylmethanaminium iodide An ion exchange column containing 150 g Dowex ®1-8X was washed with 1N sodium hydroxide, distilled water (until neutral), 1N hydriodic acid, and distilled water (until neutral). A 20 g (0.074 mol), sample of the product of Example 5 was dissolved in aqueous ethanol and placed on the top of the column. The compound was eluted through the resin with aqueous ethanol. The eluants were concentrated to give 11.2 g (~50%) N-(3-(dimethylamino)-2-ethoxy-2-propenylidene)-N-methylmethanaminium iodide as a white solid. M.p. 166°–168° C.

EXAMPLE 8
Preparation of N-(3-(diethylamino-2-ethoxy-2-propenylidene)-N-ethylethanaminium perchlorate Bromoacetaldehyde diethylacetal, 52.4 g (0.26 mol), was mixed carefully with approximately 70.7 g (0.967 mol) diethylamine and stirred at 40° C. overnight. The reaction mixture was concentrated under reduced pressure and the residue dissolved in water and basified with cold 5N sodium hydroxide. The reaction mixture was extracted twice with diethyl ether, dried over anhydrous sodium sulfate and concentrated under reduced pressure to give a tan oil. Distillation gave 35.8 g (72.8%) diethylaminoacetaldehyde diethylacetal as a clear liquid. B.p. 65°–75° C. @ 1.0 mmHg.

In a 3-neck 500 ml round-bottomed flask, 45.4 g (0.48 mol), diethylformamide, in 100 ml chloroform, was cooled to 0° C. Phosphorous oxychloride, 25 ml (0.268 mol), was added dropwise, holding the temperature below 10° C. After addition was complete, the reaction was stirred for 20 minutes. Diethylaminoacetaldehyde diethylacetal, 20 g (0.106 mol), was added. The reaction mixture was refluxed for 3 hours. The resultant orange-brown solution was poured over ice and diluted with hexane. The aqueous layer was separated and the organic layer washed once with water. Sodium perchlorate, monohydrate, 25 g (0.204 mol), was stirred into the combined aqueous layers. The brown oil which formed crystallized upon standing. Recrystallization from isopropanol gave 3.0 g (8.66%) N-(3-(diethylamino)-2-ethoxy-2-propenylidene)-N-ethylethanaminium perchlorate as an orange solid. M.p. 81°–84° C.

EXAMPLE 9
Preparation of bromoacetaldehyde methoxy propoxy acetal

N-Bromosuccinimide, 1000 g (5.6 mol), 1-propanol, 336 g (5.6 mol) and methylene chloride, 1000 ml, were placed in a 5 liter reaction flask equipped with mechanical stirrer, gas bubbler outlet, and a gas inlet tube. After cooling the mixture to −10° C. in a dry ice-acetone bath, methyl vinyl ether, 450 g (7.76 mol), was metered into the reaction flask at a rate such that almost none escaped through the bubbler outlet. The addition required 1½ hours. After addition was complete, the mixture was stirred for two hours at ambient temperature, was filtered to remove solids, and the filtrate was evaporated to yield bromoacetaldehyde methoxy propoxy acetal as a yellow oil, 937 g (85%).

NMR (CDCl$_3$): δ4.5 (t, 1H), 3.35 (m, 7H), 1.6 (sex, 2H), 0.95 (t, 3H).

EXAMPLE 10
Preparation of dimethylaminoacetaldehyde methoxy propoxy acetal

A 12 liter flask equipped with mechanical stirrer, gas inlet tube, and Dewar condenser was charged with 2000 g (10.1 mol) of bromoacetaldehyde methoxy propoxy acetal and 6000 g of DMF. The solution was cooled to −15° C. in a dry ice-acetone bath and dimethylamine, 1500 g (34 mol), was bubbled into the reaction mixture over a 2 hour period. A reaction temperature of −10° to −15° C. was maintained throughout the addition to prevent loss of dimethylamine from the solution. After addition was complete, the cooling bath was removed and the reaction mixture was allowed to warm slowly to ambient temperature.

The reaction was monitored by vapor phase chromatography. After 14 hours, the mixture contained 62% product and 38% starting material. An additional 300 g of dimethylamine were added and stirring was continued for 8 hours. At this time, analysis showed that the mixture contained greater than 95% product. The mixture was poured into an equal volume of water, and the aqueous solution was extracted with hexane. Evaporation of the hexane layer yielded dimethylaminoacetaldehyde methoxy propoxy acetal as a yellow oil, 1144 g, (70%). Its NMR spectrum was satisfactory and the product was used in the next step without further purification.

NMR (CDCl$_3$): δ4.5 (t, 1H), 3.3 (m, 5H), 2.3 (m, 8H), 1.6 (2H), 0.95 (t, 3H).

EXAMPLE 11

Preparation of
N-(3-(dimethylamino)-2-(n-propoxy)-2-propenylidene)-
N-methylmethanaminium perchlorate Dimethylformamide, 1250 ml (16.1 mol), was placed in a 12 l flask and phosphoryl chloride, 733 ml (8.0 mol), was added with stirring at a rate such that the reaction temperature reached 90° C. Dimethylaminoacetylaldehyde methoxy propoxy acetal, 650 g, (4.0 mol), was slowly dripped into the mixture. A heavy white vapor formed in the airspace above the solution during the addition, and the flask was purged periodically with nitrogen to allow visual inspection of the reaction mixture. By a combination of adjustment of the rate of addition and intermittent cooling of the reaction mixture with an ice bath, the reaction temperature was maintained between 90° and 100° C. The addition was complete in 40 minutes. The reaction remained totally under control throughout the addition, and there was no delayed exothermic reaction after the addition was complete. The mixture was stirred for 1 hour at 90° C., then allowed to cool. The black mixture was poured over 2500 g of ice with stirring. A solution of sodium perchlorate, 1100 g in 1500 ml of water, was added and, after approximately 30 seconds, the solution turned into a heavy slush. Filtration of this mixture followed by several ice water washings yielded 630 g (55%) of N-(3-(dimethylamino)-2-(n-propoxy)-2-propenylidene)-N-methylmethanaminium perchlorate as a fluffy tan solid. M.p. 119°–120° C.

EXAMPLE 12

Preparation of
N-(3-(dimethylamino)-2-(n-propoxy)-2-propenylidene-
N-methylmethanaminium iodide To a solution of potassium iodide, 1500 g (9.0 mol), in 3500 ml of water was added 1200 g of the product of Example 11. The perchlorate salt quickly went into solution and was replaced by a fine precipitate of potassium perchlorate. The mixture was stirred at ambient temperature for 1 hour, filtered, and the aqueous phase was extracted with methylene chloride (2×3000 ml). The organic phase was separated, dried over magnesium sulfate, and evaporated to yield 1400 g of a brown oil that slowly crystallized on standing. The entire mixture was dissolved in 2000 ml of isopropanol, treated with charcoal, filtered, and allowed to recrystallize. After cooling to −20° C. overnight, the product was collected by filtration, washed several times with ethyl acetate and dried in vacuo to yield 920 g of pink crystalline solid N-(3-dimethylamino)-2-(n-propoxy)-2-propenylidene)-N-methylmethanaminium iodide which was recrystallized from methanol. M.p. 133°–134° C.

EXAMPLE 13

Preparation of
N-[3-(dimethylamino)-2-(n-propoxy)-2-propenylidene[-
N-methylmethanaminium camsylate Five (5) g (0.017 mol) of the product of Example 11 was dissolved in 4 ml of absolute alcohol by warming on a water-bath to 70° C. Five (5) g (0.0185 mol) of potassium camsylate was dissolved in 4 ml of water, warmed to 70° C. and added to the perchlorate solution while warm (60° C.), stirring until a clear solution resulted. The solution was sonified for 15 minutes to assure the complete precipitation of potassium perchlorate. Another portion of 20 ml absolute alcohol was added and the content placed in a refrigerator overnight. The potassium perchlorate was filtered off with suction and the filtrate concentrated to dryness on a water bath. The solids were extracted with methylene chloride and filtered, and the solution concentrated to dryness. The residue was extracted with ethyl acetate, and the solution cooled and filtered to yield N-[3-(dimethylamino)-2-(n-propoxy)-2-propenylidene]-N-methylmethanaminium camsylate as leafy crystalline solids (yield 71%). M.p. 187° C.

EXAMPLE 14

Preparation of
N-(3-(dimethylamino)-2-n-butoxy)-N-methylmethanaminium perchlorate A mechanically stirred slurry of 206 g (1.72 mol) N-bromosuccinimide, 157.4 ml (1.72 mol) n-butanol, and 500 ml carbon tetrachloride was cooled to 0° C. Methyl vinyl ether, 100 g (1.72 mol), was bubbled slowly into the slurry, causing a mild exotherm. After approximately 2 hours, all the N-bromosuccinimide was converted to succinimide, indicating the reaction had gone to completion. The succinimide was filtered off and washed with carbon tetrachloride. The filtrate was concentrated under reduced pressure, giving 284 g (~79%) of the β-bromoacetal as a clear oil. Anhydrous dimethylamine was bubbled into a solution of 280 g (1.33 mol) of the β-bromoacetal dissolved in 250 ml ethyl ether. After approximately 50 hours, the dimethylamine hydrobromide was filtered off and washed with ether. The filtrate was concentrated under reduced pressure to give a dark liquid which was distilled at 30° C. @ ~0.5 mmHg to give 167.8 g (72%) of the β-dimethylaminoacetal as a clear liquid.

A sample of 192.3 g (2.631 mol) dimethylformamide was cooled to 0° C. and 136 ml (1.042 mol) phosphorus oxychloride was added cautiously, keeping the temperature below 10° C. The resulting solution was stirred without cooling for approximately 20 minutes. The β-dimethylaminoacetal, 100 g (0.571 mol), was added dropwise, resulting in a mild exotherm. The reaction was heated to ~80° C., at which time the reaction exothermed fairly rapidly. An ice bath was applied to return the dark reaction mixture to 80° C. The reaction was kept between 70° and 80° C. with heating for 3 hours. The mixture was poured onto a large quantity of ice and 163.8 g (1.338 mol) sodium perchlorate monohydrate was added with stirring. The resulting yellow solid was collected by vacuum filtration and recrystallized from isopropyl alcohol to give N-(3-(dimethylamino)-2-(n-butoxy)-N-methylmethanaminium perchlorate as a white solid. M.p. 110°–112° C.

EXAMPLE 15

Preparation of
N-(3-(dimethylamino)-2-(n-butoxy)-2-propenylidene)-
N-methylmethanaminium iodide A 6.0 g (0.02 mol) sample of the product of Example 14 was dissolved in a small amount of methylene chloride. This solution was shaken twice with a concentrated aqueous solution of sodium iodide. The organic layers were combined, dried over anhydrous sodium sulfate and concentrated under reduced pressure to give N-(3-(dimethylamino)-2-(n-butoxy)-2-propenylidene)-N-methylmethanaminium iodide as a white solid. M.p. 98°–110° C.

EXAMPLE 16

When, in the procedure of Example 9, the listed intermediate alcohol was substituted for propanol, subsequent reactions according to Examples 10 and 11 yielded the following perchlorate salts.

| Product | Intermediate Alcohol | Melting Point, °C. |
|---|---|---|
| (a) N—(3-(Dimethylamino)-2-methoxy-2-propenylidene)-N—methylylmethanaminium perchlorate | Methanol | 88–90 |
| (b) N—(3-(Dimethylamino)-2-isopropoxy-2-propenylidene)-N—methylmethanaminium perchlorate | Isopropanol | 89–92 |
| (c) N—(3-(Dimethylamino)-2-iso-butoxy-2-propenylidene)-N—methylmethanaminium perchlorate | Isopropanol | 93–95 |
| (d) N—(3-(Dimethylamino)-2-(1-methylpropoxy)-2-propenylidene)-N—methylmethanaminium perchlorate | 2-Butanol | 75–78 |
| (e) N—(3-(Dimethylamino)-2-pentloxy-2-propenylidene)-N—methylmethanaminium perchlorate | 1-Pentanol | 75–77 |
| (f) N—(3-(Dimethylamino)-2-(2,2-dimethylpropoxy)-2-propenylidene)-N—methylmethanaminium perchlorate | Neopentyl alcohol | 129–131 |
| (g) N—(3-(Dimethylamino)-2-hexyloxy-2-propenylidene)-N—methylmethanaminium perchlorate | 1-Hexanol | oil |
| (h) N—(3-(Dimethylamino)-2-cyclohexyloxy-2-propenylidene)-N—methylmethanaminium perchlorate | Cyclohexanol | 136–137 |
| (i) N—(3-(Dmethylamino)-2-cyclopropylmethoxy-2-propenylidene)-N—methylmethanaminium perchlorate | Cyclopropanemethanol | 95–97 |
| (j) N—(3-(Dimethylamino)-2-phenoxy-2-propenylidene)-N—methylmethanaminium perchlorate | Phenol | 129–132 |

EXAMPLE 17

| Direct Compression Tabletting | | |
|---|---|---|
| Ingredient | % Of Composition | mg per Tablet |
| N—[3-(Dimethylamino)-2-(n-propoxy)-2-propenylidene]-N—methylmethanaminium camsylate | 30.0 | 100.00 |
| Micronized cellulose pH 102 | 30.0 | 83.35 |
| Lactose, anhydrous | 42.5 | 141.65 |
| Magnesium Stearate | 2.0 | 6.65 |
| Cab-O-Sil ® (silica) | 0.5 | 1.65 |
| TOTAL | 100.0 | 333.30 |

All ingredients except the magnesium stearate are blended for 25 minutes. The magnesium stearate is screened and blended with the mixture for an additional 5 minutes, and the mixture compressed to form 13/32 inch tablets.

EXAMPLE 18

| Preparation of Tablets by Wet Granulation | | |
|---|---|---|
| Ingredient | % Of Composition | mg per Tablet |
| N—[3-(Dimethylamino)-2-(n-propoxy)-2-propenylidene]-N—methylmethanaminium camsylate | 85.0 | 500.00 |
| Starch | 1.7 | 10.0 |
| Polyvinylpyrrolidone (8% Alcohol Solution) | 2.4 | 14.0 |
| Micronized cellulose pH 101 | 10.2 | 60.0 |
| Magnesium Stearate | 0.7 | 4.0 |
| TOTAL | 100.0 | 588.0 |

The camsylate salt and starch are mixed together and granulated with the alcoholic PVP solution. The wet mass is passed through a 12 mesh screen and dried at 120° C. The dried granulation is passed through a 16 mesh screen and mixed with the micronized cellulose and magnesium stearate, which have previously been screened through a 40 mesh screen. The mixture is compressed into 7/16 inch tablets.

We claim:

1. A method for lowering elevated blood glucose levels in a patient in need thereof which comprises internal administration of a hypoglycemically effective dose of a compound of the formula

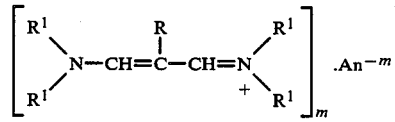

wherein R represents a group of formula $R^3X$—; $R^1$ is methyl or ethyl; $R^3$ is selected from the group consisting of straight or branched chain alkyl having from 1 to 12 carbon atoms, straight or branched chain alkenyl having from 2 to 12 carbon atoms, cycloalkyl having from 3 to 8 carbon atoms, cycloalkylalkyl having from 4 to 10 carbon atoms, benzyl, or phenyl, optionally substituted by from 1 to 3 substituents selected from the group consisting of lower alkyl, lower alkoxy, halogen, hydroxy, benzyloxy, di(lower alkyl)amino, nitro, phenyl or benzyl or by a single 2,3- or 3,4-methylenedioxy moiety; X is an oxygen atom, or a divalent sulfur atom, An is a pharmaceutically acceptable anion, and m is an integer corresponding to the valence of the anion.

2. The method of claim 1 wherein R represents the group $R^3S$—.

3. The method of claim 1 wherein R represents the group $R^3O$—.

4. The method of claim 3 wherein $R^3$ is n-propyl.

5. The method of claim 1 wherein the compound is a pharmaceutically acceptable N-(3-(dimethylamino)-2-n-propoxy-2-propenylidene)-N-methylmethanaminium salt.

6. The method of claim 1 wherein the compound is administered orally.

7. A hypoglycemic composition in solid unit dosage form which comprises a hypoglycemically effective dose of a compound of the formula

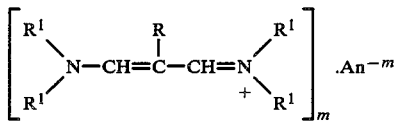

wherein R represents a group of formula $R^3X-$; $R^1$ is methyl or ethyl; $R^3$ is selected from the group consisting of straight or branched chain alkyl having from 1 to 12 carbon atoms, straight or branched chain alkenyl having from 2 to 12 carbon atoms, cycloalkyl having from 3 to 8 carbon atoms, cycloalkylalkyl having from 4 to 10 carbon atoms, benzyl, or phenyl optionally substituted by from 1 to 3 substituents selected from the group consisting of lower alkyl, lower alkoxy, halogen, hydroxy, benzyloxy, di(lower alkyl)amino, nitro, phenyl or benzyl or by a single 2,3- or 3,4-methylenedioxy moiety; X is an oxygen atom, or a divalent sulfur atom, An is a pharmaceutically acceptable anion, and m is an integer corresponding to the valence of the anion, in a pharmaceutical carrier.

8. A composition of claim 7 in a form suitable for oral administration.

9. A composition of claim 7 wherein the compound is a pharmaceutically acceptable N-(3-(dimethylamino)-2-n-propoxy-2-propenylidene)-N-methylmethanaminium salt.

* * * * *